US008802920B2

(12) United States Patent
McQuillan et al.

(10) Patent No.: US 8,802,920 B2
(45) Date of Patent: *Aug. 12, 2014

(54) ACELLULAR TISSUE MATRICES MADE FROM α-1,3-GALACTOSE-DEFICIENT TISSUE

(71) Applicant: LifeCell Corporation, Branchburg, NJ (US)

(72) Inventors: David J. McQuillan, Doylestown, PA (US); Edward S. Griffey, Fair Oaks Ranch, TX (US); Herbert Daniel Beniker, San Antonio, TX (US); Hui Xu, Plainsboro, NJ (US)

(73) Assignee: LifeCell Corporation, Branchburg, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/678,924

(22) Filed: Nov. 16, 2012

(65) Prior Publication Data

US 2013/0071486 A1    Mar. 21, 2013

Related U.S. Application Data

(63) Continuation of application No. 12/883,515, filed on Sep. 16, 2010, now Pat. No. 8,324,449, which is a continuation of application No. 10/896,594, filed on Jul. 21, 2004, now abandoned.

(60) Provisional application No. 60/489,245, filed on Jul. 21, 2003.

(51) Int. Cl.
| *A01K 67/027* | (2006.01) |
| *A61F 2/08* | (2006.01) |
| *A61L 27/36* | (2006.01) |
| *A61F 2/00* | (2006.01) |
| *C07K 16/18* | (2006.01) |
| *G01N 33/68* | (2006.01) |

(52) U.S. Cl.
CPC ........... *A61L 27/3604* (2013.01); *A61F 2/0063* (2013.01); *C07K 16/18* (2013.01); *G01N 33/6854* (2013.01)
USPC ....... 800/17; 623/11.11; 623/13.11; 623/2.11

(58) Field of Classification Search
CPC .................. A01K 2217/075; A01K 2227/108; A01K 2267/025; A61K 35/12; A61L 27/3604; A61L 27/3683; A61L 2430/36; A61L 27/507; A61B 17/0057; A61F 2/0063; C07K 16/18; C12Y 204/01087; G01N 33/6854
See application file for complete search history.

(56) References Cited

U.S. PATENT DOCUMENTS

| 4,801,299 | A | 1/1989 | Brendel et al. |
| 5,336,616 | A | 8/1994 | Livesey et al. |
| 5,821,117 | A | 10/1998 | Sandrin et al. |
| 5,846,715 | A | 12/1998 | Purcell et al. |
| 5,849,991 | A | 12/1998 | D'Apice et al. |
| 6,096,347 | A | 8/2000 | Geddes et al. |
| 6,099,567 | A | 8/2000 | Badylak et al. |
| 6,130,062 | A | 10/2000 | Milland et al. |
| 6,153,428 | A | 11/2000 | Gustafsson et al. |
| 6,166,288 | A | 12/2000 | Diamond et al. |
| 6,331,658 | B1 | 12/2001 | Cooper et al. |
| 6,371,992 | B1 | 4/2002 | Tanagho et al. |
| 6,413,769 | B1 | 7/2002 | Gustafsson et al. |
| 6,423,316 | B1 | 7/2002 | Riesbeck et al. |
| 6,432,710 | B1 | 8/2002 | Boss et al. |
| 6,455,037 | B1 | 9/2002 | Ioannou et al. |
| 6,482,404 | B1 | 11/2002 | White et al. |
| 6,495,735 | B1 | 12/2002 | White et al. |
| 6,783,776 | B2 | 8/2004 | Spievack |
| 6,849,448 | B1 | 2/2005 | D'Apice et al. |
| 6,933,326 | B1 | 8/2005 | Griffey et al. |
| 7,001,998 | B2 | 2/2006 | McKenzie et al. |
| 7,126,039 | B2 | 10/2006 | Denning et al. |
| 7,201,899 | B2 | 4/2007 | d'Apice et al. |
| 7,368,284 | B2 | 5/2008 | Koike |
| 7,432,344 | B1 | 10/2008 | Lechler et al. |
| 8,324,449 | B2 * | 12/2012 | McQuillan et al. ............. 800/17 |
| 2003/0014770 | A1 | 1/2003 | Gustafsson et al. |
| 2003/0035843 | A1 | 2/2003 | Livesey et al. |
| 2003/0068818 | A1 | 4/2003 | Denning et al. |
| 2003/0092174 | A1 | 5/2003 | Liljedahl et al. |
| 2003/0131365 | A1 | 7/2003 | Cooper et al. |
| 2003/0143207 | A1 | 7/2003 | Livesey et al. |

(Continued)

FOREIGN PATENT DOCUMENTS

| EP | 0 770 137 B1 | 2/2003 |
| EP | 1 000 161 B1 | 2/2006 |

(Continued)

OTHER PUBLICATIONS

"Highlights of the 6th Congress of the International Xenotransplantation Association, Chicago, 2001" *Xenotransplantation* 9:81-90 (2002).

(Continued)

*Primary Examiner* — Deborah Crouch
(74) *Attorney, Agent, or Firm* — McCarter & English, LLP; Matthew R. Van Eman

(57) ABSTRACT

The invention provides acellular tissue matrices made from collagen-containing tissues of animals genetically modified so as to be deficient in the galactose 1,3-galactose epitope and methods of making and using such acellular tissue matrices.

20 Claims, 4 Drawing Sheets

(56) References Cited

U.S. PATENT DOCUMENTS

| | | |
|---|---|---|
| 2003/0159161 A1 | 8/2003 | Graham et al. |
| 2003/0165480 A1 | 9/2003 | Zhu |
| 2003/0203427 A1 | 10/2003 | Koike |
| 2004/0006395 A1 | 1/2004 | Badylak |
| 2004/0064842 A1 | 4/2004 | Graham et al. |
| 2004/0115616 A1 | 6/2004 | Holton |
| 2004/0171155 A1 | 9/2004 | d'Apice et al. |
| 2004/0175366 A1 | 9/2004 | Badylak |
| 2004/0176855 A1 | 9/2004 | Badylak |
| 2004/0180439 A1 | 9/2004 | Graham et al. |
| 2004/0268424 A1 | 12/2004 | Phelps |
| 2005/0028228 A1 | 2/2005 | McQuillan et al. |
| 2005/0076399 A1 | 4/2005 | Lee et al. |
| 2005/0118160 A1 | 6/2005 | Riesbeck et al. |
| 2005/0120400 A1 | 6/2005 | Day et al. |
| 2005/0155095 A1 | 7/2005 | Koike |
| 2005/0260176 A1 | 11/2005 | Ayares et al. |
| 2005/0266561 A1 | 12/2005 | Wells |
| 2006/0068479 A1 | 3/2006 | Koike |
| 2006/0073592 A1 | 4/2006 | Sun et al. |
| 2006/0210960 A1 | 9/2006 | Livesey et al. |
| 2006/0242722 A1 | 10/2006 | Hawley |
| 2006/0294610 A1 | 12/2006 | Koike |
| 2007/0089178 A1 | 4/2007 | Zhu |
| 2007/0248575 A1 | 10/2007 | Connor et al. |
| 2008/0250517 A1 | 10/2008 | Colman et al. |
| 2009/0049562 A1 | 2/2009 | Koike |

FOREIGN PATENT DOCUMENTS

| | | |
|---|---|---|
| EP | 1 073 737 B1 | 2/2007 |
| EP | 1 141 265 B1 | 9/2008 |
| WO | WO 95/20661 A1 | 8/1995 |
| WO | WO 95/28412 A1 | 10/1995 |
| WO | WO 95/34202 A1 | 12/1995 |
| WO | WO 99/44533 A1 | 9/1999 |
| WO | WO 99/65470 A1 | 12/1999 |
| WO | WO 01/88096 A2 | 11/2001 |
| WO | WO 02/074948 A2 | 9/2002 |
| WO | WO 02/088351 A1 | 11/2002 |

OTHER PUBLICATIONS

Badylak, S. F. "Extracellular Matrix as a Biological Scaffold Material" *Acta Biomaterialia* 5:1-13 (2009).

Bello, Y.M. et al. "Tissue-Engineered Skin. Current Status in Wound Healing" *Am. J. Clin. Dermatol.* 2(5):305-313 (2001).

Chaplin, J.M. et al. "Use of an Acellular Dermal Allograft for Dural Replacement: An Experimental Study" *Neurosurgery* 45(2):320-327 (1999).

Dejardin, L.M. et al. "Tissue-Engineered Rotator Cuff Tendon Using Porcine Small Intestine Submucosa. Histologic and Mechanical Evaluation in Dogs" *Am. J. Sports Med.* 29(2):175-184 (2001).

Dejardin, L.M. et al. "Use of small intestinal submucosal implants for regeneration of large fascial defects: An experimental study in dogs" *J. Biomed. Mater. Res.* 46:203-211 (1999).

Denning et al., "Deletion of the alpha(1,3)galactosyl transferase (GGTA1) gene and the prion protein (PrP) gene in sheep," Nat. Biotech. 19:559-5562 (2001).

Denning et al., "Gene Targeting in Primary Fetal Fibroblasts from Sheep and Pig," Cloning and Stem Cells 3:221-231 (2001).

Denning et al., "New Frontiers in Gene Targeting and Cloning: Success, Application and Challenges in Domestic Animals and Human Embryonic Stem Cells," Reproduct. 126:1-11 (2003).

Krejci, N. C. et al. "In Vitro Reconstitution of Skin: Fibroblasts Facilitate Keratinocyte Growth and Differentiation on Acellular Reticular Dermis" *J Invest Dermatol* 97:843-848 (1991).

Liotta, L.A. et al. "New Method for Preparing Large Surfaces of Intact Human Basement Membrane for Tumor Invasion Studies" *Cancer Letters* 11:141-152 (1980).

Mirsadraee, S. et al. "Biocompatibility of Acellular Human Pericardium" *J. Surg. Res.* 143:407-414 (2007).

Office Action issued in U.S. Appl. No. 10/165,790, mailed on Apr. 10, 2009.

Office Action issued in U.S. Appl. No. 12/883,515, mailed on Jan. 4, 2012.

Orfila et al., "Immunofluorescent Deposits on the Tubular Basement Membrane in Human Renal Transplant," Nephron. 57:149-155 (1991).

Partial File History from U.S. Appl. No. 11/083,393, filed Mar. 17, 2005.

Phelps et al. "Production of $\alpha$ 1,3-Galactosyltransferase-Deficient Pigs," *Science* 299:411-414 (2003).

Raeder, R.H. et al. "Natural anti-galactose $\alpha$1,3 galactose antibodies delay, but do not prevent the acceptance of extracellular matrix xenografts" *Transplant Immunol.* 10:15-24 (2002).

Sandrin, M.S. et al. "Enzymatic remodelling of the carbohydrate surface of a xenogenic cell substantially reduces human antibody binding and complement-mediated cytolysis" *Nature Medicine* 1(12):1261-1267 (1995).

Sandrin, M.S. et al. "Gal$\alpha$(1,3)Gal, the Major Xenoantigen(s) Recognized in Pigs by Human Natural Antibodies" *Immunological Reviews* 141:169-190 (1994).

Sandrin, M.S. et al. "Recent advances in xenotransplantation" *Curr. Opin. Immunol.* 11:527-531 (1999).

Sharma, A. et al. "Reduction in the level of Gal($\alpha$1,3)Gal in transgenic mice and pigs by the expression of an $\alpha$(1,2)fucosyltransferase" *Proc. Natl. Acad. Sci. USA* 93:7190-7195 (1996).

Soroka et al., "Immunogenicity of Intestinal Basement Membrane," Surv. Immunol. Res. 3:264-273 (1984).

Stone, K.R. et al. "Porcine Cartilage Transplants in the Cynomolgus Monkey. III. Transplantation of $\alpha$-Galactosidase-Treated Porcine Cartilage" *Transplantation* 65(12):1577-1583 (1998).

Supplementary European Search Report issued in EP 04779040 (Date of Search: May 15, 2009; Mailing Date: Jul. 7, 2009).

Tajima, K. et al. "Regeneration through Nerve Allografts in the Cynomolgus Monkey (*Macaca fascicularis*)" *The Joural of Bone and Joint Surgery* 2:73-A (1991).

Taylor, S.G. et al. "Reduction of $\alpha$-Gal expression by relocalizing $\alpha$-galactosidase to the *trans*-Golgi network and cell surface" *Glycobiology* 12(11):729-739 (2002).

Tearle, R.G. et al. "The [alpha]-1,3-Glactosyltransferase Knockout Mouse: Implications for Xenotransplantation" *Transplantation* 61(1):13-19 (1996).

Thall, A.D. et al. "Oocyte Gal$\alpha$1,3Gal Epitopes Implicated in Sperm Adhesion to the Zona Pellucida Glycoprotein ZP3 Are Not Required for Fertilization in the Mouse" *J. Biol. Chem.* 270(37):21437-21440 (1995).

Xu et al. "A Porcine-Derived Acellular Dermal Scaffold That Supports Soft Tissue Regeneration: Removal of Terminal Glactose-$\alpha$-(1,3)-Glactose and Retention of Matrix Structure" *Tissue Engineering: Part A* 15(00):1-13 (2009).

Zheng, M.H. et al. "Porcine Small Intestine Submucosa (SIS) Is Not an Acellular Collagenous Matrix and Contains Porcine DNA: Possible Implications in Human Implantation" *J. Biomed. Mater. Res. Part B: Appl. Biomater.* 73B:61-67 (2005).

\* cited by examiner

A

B

C

D

Legend: 0 day, 7 day, 21 day, 35 day

A
XenoDerm implant

Monkey serum 5093

B
GalDerm implant

Monkey serum 6015

C
AlloDerm implant

Monkey serum 5124

Monkey serum 5136

Monkey serum 6014

Monkey serum 5119

Monkey serum 5086

Monkey serum 5098

Monkey serum 5144

ACELLULAR TISSUE MATRICES MADE FROM α-1,3-GALACTOSE-DEFICIENT TISSUE

This application is a continuation of U.S. application Ser. No. 12/883,515, filed Sep. 16, 2010, which is a continuation of U.S. application Ser. No. 10/896,594, filed Jul. 21, 2004, which claims the benefit of U.S. Provisional Application No. 60/489,245, filed Jul. 21, 2003, all of which are incorporated herein by reference.

TECHNICAL FIELD

This invention relates to tissue matrices for tissue repair, and more particularly to acellular tissue matrices made from animals genetically modified so that their tissues are deficient in the galactose α-1,3 galactose epitope.

BACKGROUND

A major problem of xenotransplantation in recipient animals (e.g., humans) that do not express the enzyme UDP-galactose: β-D-galactosyl-1,4-N-acetyl-D-glucosaminide α-1,3 galactosyl-transferase (α-1,3 galactosyltransferase; "αGT") that catalyzes the formation of the terminal disaccharide structure, galactose α-1,3 galactose ("αgal"), is the hyperacute rejection of xenografts in such recipients that is largely, if not exclusively, due to the action of antibodies specific for the αgal epitope on the surface of cells in the xenograft. Transgenic animals (e.g., pigs) have been derived which lack, or substantially lack, functional αGT and thus also lack, or substantially lack, αgal epitopes.

SUMMARY

The invention is based in part on the discovery that acellular dermal matrices (ADM) made from transgenic pigs in which both alleles of the gene encoding αGT have been disrupted such that the pigs lack the predominant αGT activity (and thus αgal epitopes on the surface of cells and on proteins of the extracellular matrix) did not stimulate the production of αgal-specific antibodies and were not infiltrated by inflammatory cells subsequent to implantation in Old World primates. The invention thus provides acellular tissue matrices made from animals (e.g., pigs) genetically modified so as to lack, or substantially lack, αgal epitopes and methods of making and using such matrices. Appropriate genetically modified animals will preferably be αGT gene-disrupted animals, i.e., animals in which both alleles of the αGT gene have been disrupted in all cells of the animal. For convenience, αGT gene-disrupted animals are referred to herein as "GTδ" animals and animals that naturally lack functional αGT protein are referred to as "GT−" animals. Animals that naturally express functional αGT protein are sometimes referred to as "GT+" animals.

More specifically, the invention features an acellular tissue matrix that includes: a decellularized collagen-containing tissue, or a decellularized collagen-containing organ, of an animal genetically modified such that tissues in the animal lack, or substantially lack, galactose α-1,3-galactose epitopes. The acellular tissue matrix preferably lacks, or substantially lacks, epithelial basement membrane. The animal can be, for example, a pig. The tissue or organ can include, for example, dermis, fascia, pericardium, dura, umbilical cord, placenta, cardiac valve, ligament, tendon, artery, vein, neural connective tissue, intestine, bladder, or ureter. The acellular tissue matrix can be in non-particulate or in particulate form. The genetic modification can include a disruption of both alleles of an α-1,3 galactosyl transferase (αGT) gene.

Also embodied by the invention is a method of making an acellular tissue matrix. The method includes: (a) providing a collagen-containing tissue or a collagen-containing organ from an animal genetically modified so that tissues in the animal lack, or substantially lack, galactose α-1,3-galactose epitopes; and (b) processing the tissue or organ to so as to render the tissue or organ acellular and lacking, or substantially lacking, in epithelial basement membrane, the processing resulting in the production of an acellular tissue matrix. The animal can be a pig and the tissue or organ can any of the above-recited tissues or organs. The genetic modification can include a disruption of both alleles of an α-1,3 galactosyl transferase (αGT) gene. The method can further include freezing and/or freeze-drying the acellular tissue matrix. Moreover, the method can further include: (a) pulverizing the acellular tissue matrix; or (b) rendering the acellular tissue matrix particulate in form. The processing can include removing and discarding an epithelium (e.g., epidermis).

Another aspect of the invention is a method of treatment. The method includes: (a) identifying a mammalian subject as having an organ, or tissue, in need of repair or amelioration; and (b) placing a composition comprising the above-described acellular tissue matrix in or on the organ or tissue. The subject can be, e.g., a human and the animal can be, e.g., a pig. The tissue or organ can be any of those recited above and the acellular tissue matrix can be non-particulate or particulate in form. The genetic modification can include disruption of both alleles of an α-1,3 galactosyl transferase (αGT) gene. The method can further comprise administration to the subject of one or more agents, e.g., a cell growth factor, an angiogenic factor, a differentiation factor, a cytokine, a hormone, or a chemokine. The one or more agents can be in the composition placed in the subject or they can be injected or infused into the subject separately from the composition. The organ or tissue of the subject can be, without limitation, skin, bone, cartilage, meniscus, dermis, myocardium, periosteum, artery, vein, stomach, small intestine, large intestine, diaphragm, tendon, ligament, neural tissue, striated muscle, smooth muscle, bladder, urethra, ureter, gingival, or fascia (e.g., abdominal wall fascia). The composition can further include demineralized bone powder. The gingiva can be, or can be proximal to, receding gingival. Moreover, the gingiva can contain a dental extraction socket.

As used herein, the term "placing" a composition includes, without limitation, setting, injecting, infusing, pouring, packing, layering, spraying, and encasing the composition. In addition, placing "on" a recipient tissue or organ means placing in a touching relationship with the recipient tissue or organ.

As used herein, a "genetically modified" animal is an animal whose genome contains an artificially inserted exogenous nucleic acid sequence or whose genome is artificially manipulated so as to lack a wild-type nucleic acid sequence. Thus, a genetically modified animal is not one in which an exogenous sequence in its genome or the absence of a wild-type nucleic acid sequence from its genome is derived by only a breeding program as is used in, for example, the generation of congenic animal strains. In addition, a genetically modified animal is not one into whose genome a wild-type viral nucleic acid sequence has integrated in the course of a viral infection. Genetically modified animals include the progeny of the manipulated animal who carry the modification in their genomes.

As used herein, the tissues in "an animal that is genetically modified such that the tissues in the animal substantially lack αgal epitopes" contain less than 5% (e.g., less than: 4%; 2%; 1%; 0.1%; 0.01%; 0.001%; or even less than 0.001%) of the αgal epitopes that corresponding tissues in a corresponding wild-type animal contain.

As used herein, the term "operably linked" means incorporated into a genetic construct so that expression control sequences (i.e., transcriptional and translational regulatory elements) effectively control expression of a coding sequence of interest. Transcriptional and translational regulatory elements include but are not limited to inducible and non-inducible promoters, enhancers, operators and other elements that are known to those skilled in the art and that drive or otherwise regulate gene expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention, e.g., acellular tissue matrices that are useful for implantation in GT− subjects (e.g., human patients), will be apparent from the following description, from the drawings and from the claims.

DESCRIPTION OF DRAWINGS

FIG. 1D shows the staining of GalDerm exposed to the secondary antibody and not to the αgal-specific monoclonal antibody.

DETAILED DESCRIPTION

Figure 1:
FIGS. 1A-1D are series of photographs showing the staining AlloDerm (FIG. 1A), XenoDerm (FIG. 1B) and GalDerm (FIG. 1C) by a monoclonal antibody specific for the αgal epitope and horseradish peroxidase-conjugated secondary antibody.
Figure 1:
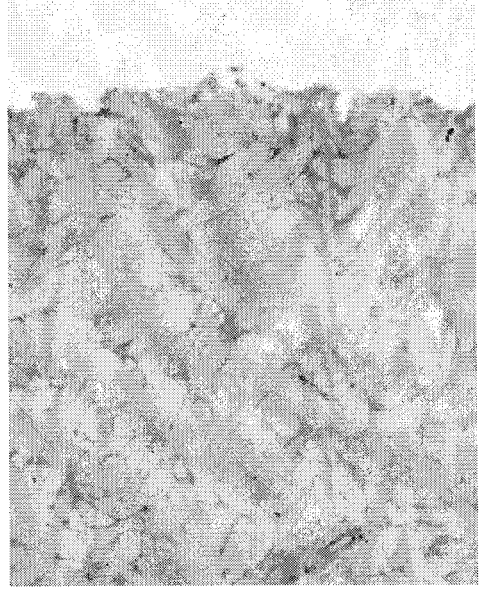
Figure 1:
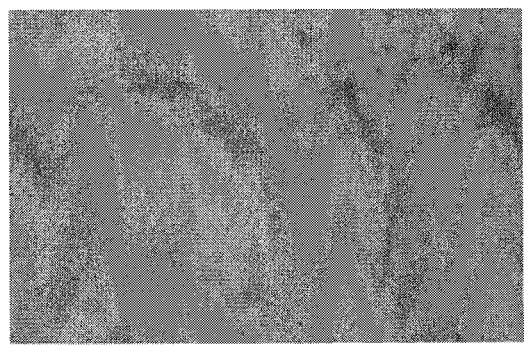
Figure 1:
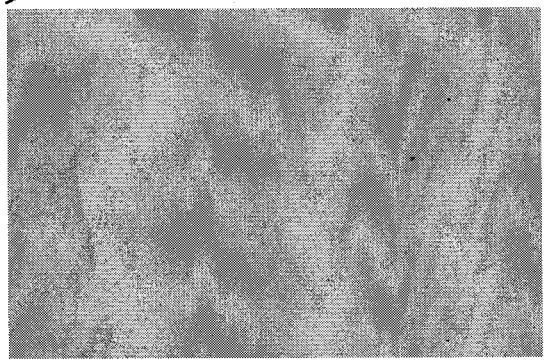

The experiments described in Examples 1-4 indicate that: (a) acellular tissue matrices produced from GTδ animals do not stimulate the production of antibodies specific for the acellular tissue matrices in GT− recipient animals into which the acellular tissue matrices have been implanted; and (b) antibodies in such GT− recipient animals do not result in an inflammatory reactions in implanted acellular tissue matrices from GTδ animals.

Various aspects of the invention are described below.
Acellular Tissue Matrices

As used herein, an "acellular tissue matrix" is a matrix that: (a) is made from any of a wide range of collagen-containing tissues; (b) is acellular (i.e., is free of intact cells, alive or dead cells); and (c) retains many of the biological and structural functions possessed by the native tissue or organ from which it was made. In addition, the acellular tissue matrices of the invention lack, or substantially lack, an epithelial basement membrane. The epithelial basement membrane is a thin sheet of extracellular material contiguous with the basilar aspect of epithelial cells. Sheets of aggregated epithelial cells form an epithelium. Thus, for example, the epithelium of skin is called the epidermis and the skin epithelial basement membrane lies between the epidermis and the dermis. The epithelial basement membrane is a specialized extracellular matrix that provides a barrier function and an attachment surface for epithelial-like cells; however, it does not contribute any significant structural or biomechanical role to the underlying tissue (e.g., dermis). Unique components of epithelial basement membranes include, for example, laminin, collagen type VII, and nidogen. The unique temporal and spatial organization of the epithelial basement membrane distinguish it from, e.g., the dermal extracellular matrix. The presence of the epithelial basement membrane in an acellular tissue matrix of the invention could be disadvantageous in that the epithelial basement membrane likely contains a variety of species-specific components that would elicit the production of antibodies, and/or bind to preformed antibodies, in xenogeneic graft recipients of the acellular matrix. In addition, the epithelial basement membrane can act as barrier to diffusion of cells and/or soluble factors (e.g., chemoattractants) and to cell infiltration. Its presence in acellular tissue matrix grafts can thus significantly delay formation of new tissue from the acellular tissue matrix in a recipient animal. As used herein, an acellular tissue matrix that "substantially lacks" an epithelial basement membrane is an acellular tissue matrix containing less than 5% (e.g., less than: 3%; 2%; 1%; 0.5%; 0.25%; 0.1%; 0.01%; 0.001%; or even less than 0.001%) of the epithelial basement membrane possessed by the corresponding unprocessed tissue from which the acellular tissue matrix was derived.

Biological functions retained by the acellular tissue matrices of the invention include cell recognition and cell binding as well as the ability to support cell spreading, cell proliferation, and cell differentiation. Such functions are provided by undenatured collagenous proteins (e.g., type I collagen) and a variety of non-collagenous molecules (e.g., proteins that serve as ligands for other molecules such as integrin receptors, molecules with high charge density such as glycosaminoglycans (e.g., hyaluronan) or proteoglycans, or other adhesins). Structural functions retained by useful acellular tissue matrices include maintenance of histological architecture, maintenance of the three-dimensional array of the tissue's components and physical characteristics such as strength, elasticity, and durability, defined porosity, and retention of macromolecules. The efficiency of the biological functions of an acellular tissue matrix can be measured, for example, by its ability to support cell proliferation and is at least 50% (e.g., at least: 50%; 60%; 70%; 80%; 90%; 95%; 98%; 99%; 99.5%; 100%; or more than 100%) of those of the native tissue or organ from which the acellular tissue matrix is made.

It is not necessary that the grafted matrix material be made from tissue that is identical to the surrounding recipient tissue but should simply be amenable to being remodeled by invading or infiltrating cells such as differentiated cells of the relevant host tissue, stem cells such as mesenchymal stem cells, or progenitor cells. Remodeling is directed by the above-described acellular tissue matrix components and signals from the surrounding host tissue (such as cytokines, extracellular matrix components, biomechanical stimuli, and bioelectrical stimuli). The presence of mesenchymal stem cells in the bone marrow and the peripheral circulation has been documented in the literature and shown to regenerate a variety of musculoskeletal tissues [Caplan (1991) J. Orthop. Res. 9:641-650; Caplan (1994) Clin. Plast. Surg. 21:429-435; and Caplan et al. (1997) Clin Orthop. 342:254-269]. Additionally, the graft must provide some degree (greater than threshold) of tensile and biomechanical strength during the remodeling process.

It is understood that an acellular tissue matrix of the invention can be produced from any collagen-containing tissue (e.g., dermis, fascia, pericardium, dura, umbilical cords, placentae, cardiac valves, ligaments, tendons, cartilage, bone, vascular tissue (arteries and veins such as saphenous veins), neural connective tissue, or ureters), as long as the above-described properties are retained by the matrix. Moreover the tissues in which the acellular tissue matrix grafts are placed include essentially any tissue that can be modeled by invading or infiltrating cells (see above). Relevant tissues include skeletal tissues such as bone, cartilage, ligaments, fascia, and tendon. Other tissues in which any of the above acellular tissue matrix grafts can be placed include, without limitation, fascia, skin, gingiva, dura, myocardium, vascular tissue, neural tissue, striated muscle, smooth muscle, bladder wall, ureter tissue, intestine, and urethra tissue. It is understood that, for the purposes of the invention, heart muscle and skeletal muscle are not the same tissue. See, U.S. Patent Application Publication No. US2004/0043006 (the disclosure of which is incorporated herein by reference in its entirety) for a description of epithelia, epithelial basement membranes, and components on the side of the epithelial basement membrane opposite to the epithelium in tissues such as urinary bladder tissue and small intestine.

The form in which the acellular tissue matrix is provided will depend on the tissue or organ from which it is derived and on the nature of the recipient tissue or organ, as well as the nature of the damage or defect in the recipient tissue or organ. Thus, for example, a matrix derived from a heart valve can be provided as a whole valve, as small sheets or strips, as pieces cut into any of a variety of shapes and/or sizes, or in a particulate form. The same concept applies to acellular tissue matrices produced from any of the above-listed tissues and organs.

Methods of Making and Using Acellular Tissue Matrices

The acellular tissue matrices of the invention can be produced by any of a variety of methods. All that is required is that the steps used in their production result in matrices with the above-described biological and structural properties. Particularly useful methods of production include those described in U.S. Pat. Nos. 4,865,871 and 5,366,616 and co-pending U.S. application Ser. Nos. 09/762,174, 10/165,790, and 10/273,780, the disclosures of which are incorporated herein by reference in their entirety.

In brief, the steps involved in the production of an acellular tissue matrix generally include harvesting the tissue from a donor (e.g., a pig or any of the species listed below), optionally slicing tissue in the horizontal plane to generate multiple sheets, removal of the epithelial basement membrane, chemical treatment so as to stabilize the tissue and avoid biochemical and structural degradation, together with or followed by cell removal under conditions which similarly preserve biological and structural function. After thorough removal of dead and/or lysed cell components below levels that may cause inflammation as well any bio-incompatible cell-removal agents, the acellular tissue matrix is in principle ready for implantation and only need be processed into a desired shape or size. Alternatively, the acellular tissue matrix can be treated with a cryopreservation agent and cryopreserved and, optionally, freeze dried, again under conditions necessary to maintain the described biological and structural properties of the matrix; after freeze drying, the tissue can be pulverized or micronized to produce a particulate acellular tissue matrix under similar function-preserving conditions. Alternatively, the acellular tissue matrix can be preserved by replacing most of the water in the tissue with an agent such as glycerol such that the acellular tissue matrix contains, for example, approximately 85% by weight glycerol; the acellular tissue matrix can be stored in this form for extended period at less than 20° C. All steps are generally carried out under aseptic, preferably sterile, conditions.

The initial stabilizing solution arrests and prevents osmotic, hypoxic, autolytic, and proteolytic degradation, protects against microbial contamination, and reduces mechanical damage that can occur with tissues that contain, for example, smooth muscle components (e.g., blood vessels). The stabilizing solution generally contains an appropriate buffer, one or more antioxidants, one or more oncotic agents, one or more antibiotics, one or more protease inhibitors, and in some cases depending on the tissue, a smooth muscle relaxant.

The tissue can then be placed in a processing solution to remove viable cells (e.g., epithelial cells, endothelial cells, smooth muscle cells, and fibroblasts) from the structural matrix without damaging the biological and structural integrity of the collagen matrix. The processing solution generally contains an appropriate buffer, salt, an antibiotic, one or more detergents, one or more agents to prevent cross-linking, one or more protease inhibitors, and/or one or more enzymes. Treatment of the tissue must be (a) with a processing solution containing active agents at a concentration and (b) for a time period such that the structural integrity of the matrix is maintained.

Where the tissue contains an epithelium (e.g., the epidermis of skin), the initial step in removing cells, prior to placement in the processing solution(s) described above, can involve physical separation of the epithelium from the rest of the tissue using methods known in the art (see, e.g., Example 1). After removal of the epithelium, all, or substantially all, the epithelial basement membrane is removed and discarded. This is achieved, for example, by mechanical cutting. Appropriate methods are familiar to those in the art and can be, for example, adaptations of methods used in the leather and tanning industries.

After the tissue is decellularized, the resulting acellular tissue matrix can be incubated in a cryopreservation solution. This solution generally contains one or more cryoprotectants (e.g., dimethyl sulfoxide or glycerol) to minimize ice crystal damage to the structural matrix that can occur during freezing. If the acellular tissue matrix is to be freeze dried, the solution will generally also contain one or more dry-protective components, to minimize structural damage during drying and may include a combination of an organic solvent and water which undergoes neither expansion or contraction during freezing. As an alternate method, the acellular tissue matrix can be fixed with a crosslinking agent such as glutaraldehyde and stored prior to transplantation. The cryoprotective and dry-protective agents can be the same one or more substances. If the acellular tissue matrix is not going to be freeze dried, it can be frozen by placing it (in a sterilized container) in a freezer at about −80° C., or by plunging it into sterile liquid nitrogen, and then storing at a temperature below −160° C. until use. The sample can be thawed prior to use by, for example, immersing a sterile non-permeable vessel (see below) containing in a water bath at about 37° C. or by allowing the acellular tissue matrix to come to room temperature under ambient conditions.

If the acellular tissue matrix is to be frozen and freeze dried, following incubation in the cryopreservation solution, it can be packaged inside a sterile vessel that is permeable to water vapor yet impermeable to bacteria, e.g., a water vapor permeable pouch or glass vial. One side of a preferred pouch consists of medical grade porous Tyvek® membrane, a trademarked product of DuPont Company of Wilmington, Del. This membrane is porous to water vapor and impervious to bacteria and dust. The Tyvek membrane is heat sealed to an impermeable polyethylene laminate sheet, leaving one side open, thus forming a two-sided pouch. The open pouch is sterilized by irradiation (e.g., gamma irradiation) prior to use. The acellular tissue matrix is aseptically placed (through the open side) into the sterile pouch. The open side is then aseptically heat-sealed to close the pouch. The packaged acellular tissue matrix is thenceforth protected from microbial contamination throughout subsequent processing steps.

The vessel containing the acellular tissue matrix is cooled to a low temperature at a specified rate which is compatible with the specific cryoprotectant to minimize the development of damaging hexagonal ice. See U.S. Pat. No. 5,336,616 for examples of appropriate cooling protocols. The tissue is then dried at a low temperature under vacuum conditions, such that water vapor is removed sequentially without ice recrystallization.

At the completion of the drying of the samples in the water vapor permeable vessel, the vacuum of the freeze drying apparatus is reversed with a dry inert gas such as nitrogen, helium or argon. While being maintained in the same gaseous environment, the semipermeable vessel is placed inside an impervious (i.e., impermeable to water vapor as well as microorganisms) vessel (e.g., a pouch), which is further sealed, e.g., by heat and/or pressure. Where the acellular tissue matrix is frozen and dried in a glass vial, the vial is sealed under vacuum with an appropriate inert stopper and the vacuum of the drying apparatus reversed with an inert gas prior to unloading. In either case, the final product is hermetically sealed in an inert gaseous atmosphere.

The freeze dried acellular tissue matrix can be stored under these conditions for extended time periods under ambient refrigerated conditions. Transportation may be accomplished via standard carriers and under standard conditions relative to normal temperature exposure and delivery times.

Generally (but not necessarily) the dried acellular tissue matrix is rehydrated prior to transplantation. It is important to minimize osmotic forces and surface tension effects during rehydration. The aim in rehydration is to augment the selective preservation of the extracellular support matrix. Appropriate rehydration can be accomplished by, for example, an initial incubation of the dried acellular tissue matrix in an environment of about 100% relative humidity, followed by immersion in a suitable rehydration solution. Alternatively, the dried tissue may be directly immersed in the rehydration solution without prior incubation in a high humidity environment. Rehydration should not cause osmotic damage to the sample. Vapor rehydration should ideally achieve a residual moisture level of at least 15% and fluid rehydration should result in a tissue moisture level of between 20% and 70%. Depending on the particular acellular tissue matrix to be rehydrated, the rehydration solution can be, for example, normal saline, Ringer's lactate, or a standard cell culture medium. Where the acellular tissue matrix is subject to the action of endogenous proteases, collagenases, elastases or residual autolytic activity from previously removed cells, additives to the rehydration solution are made and include protease inhibitors. Where residual free radical activity is present, agents to protect against free radicals are used including antioxidants, and enzymatic agents that protect against free radical damage. Antibiotics may also be included to inhibit bacterial contamination. Oncotic agents being in the form of proteoglycans, hyaluronan, dextran and/or amino acids may also be included to prevent osmotic damage to the matrix during rehydration. Rehydration of a dry sample is especially suited to this process as it allows rapid and uniform distribution of the components of the rehydration solution. In addition, the rehydration solutions may contain specific components not used previously, for example, diphosphonates to inhibit alkaline phosphatase and prevent subsequent calcification. Agents may also be included in the rehydration solution to stimulate neovascularization and host cell infiltration following transplantation of the rehydrated acellular tissue matrix e.g., growth-factors, cytokines, chemoattractive agents, cell-stimulatory factors, or genes.

Histocompatible, viable cells can be restored to the acellular tissue matrix to produce a permanently accepted graft that may be modeled by the host. This is generally done just prior to, or after, placing of the acellular tissue matrix in a mammalian subject. Where the acellular tissue matrix has been freeze dried, it will be done after rehydration. In a preferred embodiment, histocompatible viable cells may be added to the matrices by standard in vitro cell co-culturing techniques prior to transplantation, or by in vivo repopulation following transplantation.

The cell types used for reconstitution will depend on the nature of the tissue or organ to, or into, which the acellular tissue matrix is placed. Cells with which the matrices can be repopulated include, but are not limited to, fibroblasts, embryonic stem cells (ESC), adult or embryonic mesenchymal stem cells (MSC), prochondroblasts, chondroblasts, chondrocytes, pro-osteoblasts, osteocytes, osteoclasts, monocytes, pro-cardiomyoblasts, pericytes, cardiomyoblasts, cardiomyocytes, gingival epithelial cells, or periodontal ligament stem cells. Naturally, the acellular tissue matrices can be repopulated with combinations of two or more (e.g., two, three, four, five, six, seven, eight, nine, or ten) of these cell-types.

Following removal of cells, following freezing, following drying, following drying and rehydration, or following reconstitution of the acellular tissue matrix (whether or not frozen or dried) with appropriate cells, the acellular tissue matrix can be transported to the appropriate hospital or treatment facility. The choice of the final composition of the product will be dependent on the specific intended clinical application.

Reagents and methods for carrying out all the above steps are known in the art. Suitable reagents and methods are described in, for example, U.S. Pat. No. 5,336,616.

Particulate acellular tissue matrices can be made from any of the above described non-particulate acellular tissue matrices by any process that results in the preservation of the biological and structural functions described above and, in particular, damage to collagen fibers, including sheared fiber ends, should be minimized. Many known wet and drying processes for making particulate matrices do not so preserve the structural integrity of collagen fibers.

One appropriate method is described in co-pending U.S. patent application Ser. No. 09/762,174. The process is briefly described below with respect to a freeze dried dermal acellular tissue matrix but one of skill in the art could readily adapt the method for use with freeze dried acellular tissue matrices derived from any of the other tissues listed herein.

The acellular dermal matrix can be cut into strips (using, for example, a Zimmer mesher fitted with a non-interrupting "continuous" cutting wheel). The resulting long strips are then cut into lengths of about 1 cm to about 2 cm. A homogenizer and sterilized homogenizer probe (e.g., a LabTeck Macro homogenizer available from OMNI International, Warrenton, Va.) is assembled and cooled to cryogenic temperatures (i.e., about $-196°$ C. to about $-160°$ C.) using sterile liquid nitrogen which is poured into the homogenizer tower. Once the homogenizer has reached a cryogenic temperature, cut pieces of acellular tissue matrix are added to the homogenizing tower containing the liquid nitrogen. The homogenizer is then activated so as to cryogenically fracture the pieces of acellular tissue matrix. The time and duration of the cryogenic fracturing step will depend upon the homogenizer utilized, the size of the homogenizing chamber, and the speed and time at which the homogenizer is operated, and are readily determinable by one skilled in the art. As an alternative, the cryofracturing process can be conducted in a cryomill cooled to a cryogenic temperature.

The cryofractured particulate acellular tissue matrix is, optionally, sorted by particle size by washing the product of the homogenization with sterile liquid nitrogen through a series of metal screens that have also been cooled to a cryogenic temperature. It is generally useful to eliminate large undesired particles with a screen with a relatively large pore size before proceeding to one (or more screens) with a smaller pore size. Once isolated, the particles can be freeze dried to ensure that any residual moisture that may have been absorbed during the procedure is removed. The final product is a powder (usually white or off-white) generally having a particle size of about 1 micron to about 900 microns, about 30 microns to about 750 microns, or about 150 to about 300 microns. The material is readily rehydrated by suspension in normal saline or any other suitable rehydrating agent known in the art. It may also be suspended in any suitable carriers known in the art (see, for example, U.S. Pat. No. 5,284,655 incorporated herein by reference in its entirety). If suspended at a high concentration (e.g., at about 600 mg/ml), the particulate acellular tissue matrices can form a "putty", and if suspended at a somewhat lower concentration (e.g., about 330 mg/ml), it can form a "paste". Such putties and pastes can conveniently be packed into, for example, holes, gaps, or spaces of any shape in tissues and organs so as to substantially fill such holes, gaps, or spaces.

One highly suitable freeze dried acellular tissue matrix is produced from human dermis by the LifeCell Corporation (Branchburg, N.J.) and marketed in the form of small sheets as AlloDerm®. Such sheets are marketed by the LifeCell Corporation as rectangular sheets with the dimensions of, for example, 1 cm×2 cm, 3 cm×7 cm, 4 cm×8 cm, 5 cm×10 cm, 4 cm×12 cm, and 6 cm×12 cm. The cryoprotectant used for freezing and drying Alloderm is a solution of 35% maltodextrin and 10 mM ethylenediaminetetraacetate (EDTA). Thus, the final dried product contains about 60% by weight acellular tissue matrix and about 40% by weight maltodextrin. The LifeCell Corporation also makes an analogous product from pig dermis as XenoDerm™ having the same proportions of acellular tissue matrix and maltodextrin as AlloDerm. In addition, the LifeCell Corporation markets a particulate acellular dermal matrix made by cryofracturing AlloDerm (as described above) under the name Cymetra®. The particle size for Cymetra is in the range of about 60 microns to about 150 microns as determined by mass.

The particles of particulate or pulverized (powdered) acellular tissue matrices of the invention will be less than 1.0 mm in their longest dimension. Pieces of acellular tissue matrix with dimensions greater than this are non-particulate acellular matrices.

The form of acellular tissue matrix used in any particular instance will depend on the tissue or organ to which it is to be applied. Generally non-particulate acellular tissue matrices that are provided in dry form (e.g., AlloDerm) are rehydrated in a sterile physiological solution (e.g., saline) before use. However they can also be used dry.

Sheets of acellular tissue matrix (optionally cut to an appropriate size) can be: (a) wrapped around a tissue or organ that is damaged or that contains a defect; (b) placed on the surface of a tissue or organ that is damaged or has a defect; or (c) inserted into a cavity, gap, or space in the tissue or organ. Such cavities, gaps, or spaces can be, for example: (i) of traumatic origin (e.g. an incisional hernia or an infection-related defect), (ii) due to removal of diseased tissue (e.g., infarcted myocardial tissue), or (iii) due to removal of malignant or non-malignant tumors. The acellular tissue matrices can be used to augment or ameliorate underdeveloped tissues or organs or to augment or reconfigure deformed tissues or organs. One or more (e.g., one, two, three, four, five, six, seven, eight, nine, ten, 12, 14, 16, 18, 20, 25, 30, or more) such strips can be used at any particular site. The grafts can be held in place by, for example, sutures, staples, tacks, or tissue glues or sealants known in the art. Alternatively, if, for example, packed sufficiently tightly into a defect or cavity, they may need no securing device. Particulate acellular tissue matrices can be suspended in a sterile pharmaceutically acceptable carrier (e.g., normal saline) and injected via hypodermic needle into a site of interest. Alternatively, the dry powdered matrix or a suspension can be sprayed into or onto a site or interest. A suspension can be also be poured into or onto a particular site. In addition, by mixing the particulate acellular tissue matrix with a relatively small amount of liquid carrier, a "putty" can be made. Such a putty, or even dry particulate acellular tissue matrix, can be layered, packed, or encased in any of the gaps, cavities, or spaces in organs or tissues mentioned above. Moreover, a non-particulate acellular tissue matrix can be used in combination with particulate acellular tissue matrix. For example, a cavity in bone could be packed with a putty (as described above) and covered with a sheet of acellular tissue matrix.

It is understood that an acellular tissue matrix can be applied to a tissue or organ in order to repair or regenerate that tissue or organ and/or a neighboring tissue or organ. For example, a strip or multiple strips of acellular tissue matrix can be used to augment primary ventral hernia repairs, or for larger defects can be used to substitute for missing or excised fascia and muscle, thus providing protection and mechanical support in abdominal wall defects. A strip of acellular tissue matrix can be wrapped around a critical gap defect of a long bone to generate a periosteum equivalent surrounding the gap defect and the periosteum equivalent can in turn stimulate the production of bone within the gap in the bone. Similarly, by implanting an acellular tissue matrix in a dental extraction socket, injured gum tissue can be repaired and/or replaced and the "new" gum tissue can assist in the repair and/or regeneration of any bone in the base of the socket that may have been lost as a result, for example, of tooth extraction. In regard to gum tissue (gingiva), receding gums can also be replaced by injection of a suspension, or by packing of a putty of particulate acellular tissue matrix into the appropriate gum tissue. Again, in addition to repairing the gingival tissue, this treatment can result in regeneration of bone lost as a result of periodontal disease and/or tooth extraction. Compositions used to treat any of the above gingival defects can contain one or more other components listed herein, e.g., demineralized bone powder, growth factors, or stem cells.

Both non-particulate and particulate acellular tissue matrices can be used in combination with other scaffold or physical support components. For example, one or more sheets of acellular tissue matrix can be layered with one or more sheets made from a biological material other than acellular tissue matrix, e.g., irradiated cartilage supplied by a tissue bank such as LifeNet, Virginia Beach, Va., or bone wedges and shapes supplied by, for example, the Osteotech Corporation, Edentown, N.J. Alternatively, such non-acellular tissue matrix sheets can be made from synthetic materials, e.g., polyhydroxy-alkanoates, such as that supplied by Tepha, Inc., Boston, Mass. Other suitable scaffold or physical support materials are disclosed in U.S. Pat. No. 5,885,829, the disclosure of which is incorporated herein by reference in its entirety. It is understood that such additional scaffold or physical support components can be in any convenient size or shape, e.g., sheets, cubes, rectangles, discs, spheres, or particles (as described above for particulate acellular tissue matrices).

Other active substances that can be mixed with particulate acellular tissue matrices or impregnated into non-particulate acellular tissue matrices include bone powder, demineralized bone powder, and any of those disclosed above.

Factors that can be incorporated into the acellular tissue matrices, administered to the placement site of an acellular tissue matrix graft, or administered systemically include any of a wide range of cell growth factors, angiogenic factors, differentiation factors, cytokines, hormones, and chemokines known in the art. Any combination of two or more of the factors can be administered to a subject by any of the means recited below. Examples of relevant factors include fibroblast growth factors (FGF) (e.g., FGF1-10), epidermal growth factor, keratinocyte growth factor, vascular endothelial cell growth factors (VEGF) (e.g., VEGF A, B, C, D, and E), platelet-derived growth factor (PDGF), interferons (IFN) (e.g., IFN-$\alpha$, $\beta$, or $\gamma$), transforming growth factors (TGF) (e.g., TGF$\alpha$ or $\beta$), tumor necrosis factor-$\alpha$, an interleukin (IL) (e.g., IL-1-IL-18), Osterix, Hedgehogs (e.g., sonic or desert), SOX9, bone morphogenic proteins, parathyroid hormone, calcitonin prostaglandins, or ascorbic acid.

Factors that are proteins can also be delivered to a recipient subject by administering to the subject: (a) expression vectors (e.g., plasmids or viral vectors) containing nucleic acid sequences encoding any one or more of the above factors that are proteins; or (b) cells that have been transfected or transduced (stably or transiently) with such expression vectors. Such transfected or transduced cells will preferably be derived from, or histocompatible with, the recipient. However, it is possible that only short exposure to the factor is required and thus histo-incompatible cells can also be used. The cells can be incorporated into the acellular tissue matrices (particulate or non-particulate) prior to the matrices being placed in the subject. Alternatively, they can be injected into an acellular tissue matrix already in place in a subject, into a region close to an acellular tissue matrix already in place in a subject, or systemically. Naturally, administration of the acellular tissue matrices and/or any of the other substances or factors mentioned above can be single, or multiple (e.g., two, three, four, five, six, seven, eight, nine, 10, 15, 20, 25, 30, 35, 40, 50, 60, 80, 90, 100, or as many as needed). Where multiple, the administrations can be at time intervals readily determinable by one skilled in art. Doses of the various substances and factors will vary greatly according to the species, age, weight, size, and sex of the subject and are also readily determinable by a skilled artisan.

Conditions for which the matrices can be used are multiple. Thus, for example, they can be used for the repair of bones and/or cartilage with any of the above-described damage or defects. Both particulate and non-particulate acellular tissue matrices can be used in any of the forms and by any of the processes listed above. Bones to which such methods of treatment can be applied include, without limitation, long bones (e.g., tibia, femur, humerus, radius, ulna, or fibula), bones of the hand and foot (e.g., calcaneas bone or scaphoid bone), bones of the head and neck (e.g., temporal bone, parietal bone, frontal bone, maxilla, mandible), or vertebrae. As mentioned above, critical gap defects of bone can be treated with acellular tissue matrices. In such critical gap defects, the gaps can be filled with, example, a putty of particulate acellular tissue matrix or packed sheets of acellular tissue matrix and wrapped with sheets of acellular tissue matrix. Alternatively, the gaps can be wrapped with a sheet of acellular tissue matrix and filled with other materials (see below). In all these bone and/or cartilage treatments, additional materials can be used to further assist in the repair process. For example, the gap can be filled cancellous bone and or calcium sulfate pellets and particulate acellular tissue matrices can be delivered to sites of bone damage or bone defects mixed with demineralized bone powder. In addition, acellular tissue matrices can be combined with bone marrow and/or bone chips from the recipient.

Acellular tissue matrices can also be used to repair fascia, e.g., abdominal wall fascia or pelvic floor fascia. In such methods, strips of acellular tissue matrix are generally attached to the abdominal or pelvic floor by, for example, suturing either to the surrounding fascia or host tissue or to stable ligaments or tendons.

Infarcted myocardium is another candidate for remodeling repair by acellular tissue matrices. Contrary to prior dogma, it is now known that not all cardiac myocytes have lost proliferative and thus regenerative potential [e.g., Beltrami et al. (2001) New. Engl. J. Med. 344:1750-1757; Kajstura et al. (1998) Proc. Nat'l. Acad. Sci. USA 95:8801-8805]. Moreover, stem cells, present for example in bone marrow and blood and as pericytes associated with blood vessels, can differentiate to cardiac myocytes. Either the infarcted tissue itself can be removed and replaced with a sheet of acellular tissue matrix cut to an appropriate size or a suspension of particulate acellular tissue matrix can be injected into the infarcted tissue. Congenital heart hypoplasia, or other structural defects, can be repaired by, for example, making an incision in the tissue, expanding the gap created by the incision, and inserting a sheet of acellular tissue matrix cut to the desired size, or placing sheets of acellular tissue matrix on the epicardial and endocardial surfaces and placing particulate acellular tissue matrix between them. It is understood that, in certain conditions, creating a gap by incision may not be sufficient and it may be necessary to excise some tissue. Naturally, one of skill in the art will appreciate that the acellular tissue matrices can be used similarly to repair damage to or defects in other types of muscle, e.g., ureter or bladder or skeletal muscle such as biceps, pectoralis, or latissimus.

Moreover, sheets of acellular tissue matrix can be used to repair or replace damaged or removed intestinal tissue, including the esophagus, stomach and small and large intestines. In this case, the sheets of acellular tissue matrix can be used to repair perforations or holes in the intestine. Alternatively, a sheet of acellular tissue matrix can be formed, for example, into a cylinder, which can be used to fill a gap in the intestine (e.g., a gap created by surgery to remove a tumor or a diseased segment of intestine). Such methods can be used to treat, for example, diaphragmatic hernias. It will be understood that an acellular tissue matrix in sheet form can also be used to repair the diaphragm itself in this condition as well as in other conditions of the diaphragm requiring repair or replacement, or addition of tissue.

Donors of Tissue for Making Acellular Tissue Matrices and Recipients of Acellular Tissue Matrices The acellular tissue matrices of the invention are generally made from one or more individuals of a species other than that of the recipient of the acellular tissue matrix graft. Thus, for example, an acellular tissue matrix can be made from a pig and be implanted in a human patient. In addition, while recipients of GTδ acellular tissue matrices will generally be of a GT− species, this also is not absolutely required. Since GT+ animals express αgal epitopes they would generally be expected not to produce antibody specific for αgal epitopes. Thus, in such a recipient it is not relevant whether an acellular tissue matrix to be placed in the recipient contains αgal epitopes or not. Species that can serve as recipients of acellular tissue matrices thus include, without limitation, humans, non-human primates (e.g., monkeys, baboons, or chimpanzees), pigs, cows, horses, goats, sheep, dogs, cats, rabbits, guinea pigs, gerbils, hamsters, rats, or mice. Preferred recipients are of GT− species, e.g., humans and Old World primates (e.g. African green monkeys, cynamolgus monkeys, macaques, Vervet monkeys, and baboons). Species from which animals genetically modified so as to lack, or substantially lack, αgal epitopes can be made as a source of tissues for the production of the acellular tissue matrices of the invention include all of the above except the GT− species, i.e., human and Old World primates. A preferred genetic modification is the disruption of both alleles of the αGT gene in all the cells of such animals. Other appropriate genetically modified animals include, without limitation, α(1,2)fucosyltransferase or α(2,6)sialyltransferase transgenic animals [see, for example, U.S. Pat. No. 6,166,288; and Sharma et al. (1996) Proc. Natl. Acad. Sci. USA 93(14):7190-7195, the disclosures of which are incorporated herein by reference in their entirety].

Methods of making transgenic animals, and in particular gene-disrupted transgenic animals, are well known in the art. Indeed, both GTδ mice and GTδ pigs have been generated [see, for example: U.S. Pat. No. 5,849,991; Lai et al. (2002) Science 295(5557):1089-1092; Dai et al. (2002) Nat. Biotechnol. 20(3):251-255; Phelps et al. (2003) Science 299 (5605):411-414; and Lai et al. (2003) Cloning Stem Cells 5(4): 233-241, the disclosures of all of which are incorporated herein by reference in their entirety].

Methods of making gene-disrupted animals involve incorporating into the germline of an individual of a species a disrupted form of a gene of interest. The gene can be disrupted so that no protein product (e.g., αGT) is produced or a protein product is produced that lacks the activity, or substantially lacks the activity, of the protein. As used herein, a αGT protein "substantially lacking αGT activity" is an αGT protein that has less than 5% (e.g., less than: 4%; 2%; 1%; 0.1%; 0.01%; 0.001%; or even less than 0.001%) of the ability of wild-type αGT to generate αgal epitopes. Methods of disrupting genes, and in particular, the αGT gene, are known in the art (see above) and generally involve the process known as homologous recombination. In this process, one or both copies of a wild-type gene of interest in an appropriate target cell (see below) is/are disrupted by inserting, using an appropriate genetic construct, a sequence into the wild-type gene(s) such that no transcript is produced from the gene(s), a transcript is produced from which no protein is translated, or a transcript is produced from which a protein is produced that lacks, or substantially lacks, the activity of the protein of interest. In such constructs, there is generally all or part of the genomic sequence of the gene of interest and, within that genomic sequence, a sequence that will disrupt expression of the gene in one of the ways described above. The sequence used to disrupt expression of the gene will frequently be a sequence encoding a protein that endows antibiotic resistance (e.g., neomycin resistance) on target cells that have incorporated the construct into their genomes. Such a coding sequence facilitates the in vitro selection of cells that have incorporated the genetic construct into their genomes. Additional drug selection methodologies known in the art can be used to select cells in which recombination between the construct and at least one copy of the targeted gene has occurred.

In earlier methods of generating gene disrupted animals, totipotent cells (i.e., cells capable of giving rise to all cell types of an embryo) were used as target cells. Such cells included, for example embryonic stem (ES) cells (in the form of ES cell lines) or fertilized eggs (oocytes). A population of ES cells in which at least one copy of the gene of interest is disrupted is injected into appropriate blastocysts and the injected blastocysts are implanted into foster mothers. Alternatively, fertilized eggs injected with the gene-disrupting construct of interest are implanted in the foster mothers. Moreover, oocytes implanted in foster mothers can be those that have been enucleated and injected with nuclei from successfully gene-disrupted ES cells [Campbell et al. (1996) Nature 380: 64-66]. Resulting mutation-containing offspring arising in such mother foster mothers are identified and, from these founder animals, distinct animal lines are produced using breeding and selection methods known to those in the art.

More recently methods for making standard and gene-disrupted transgenic animals have employed somatic cells (e.g., fetal fibroblasts) as target cells for the gene-disruption (see below). Since such cells grow much faster and are more easily handled in vitro than, for example, ES cells, the gene disruption and subsequent gene-disrupted cell selection procedures are greatly facilitated using them. Having selected a line of successfully gene-disrupted somatic cells in vitro, using any of a number of procedures (e.g., cell fusion or nuclear transplantation), nuclei from the successfully gene-disrupted somatic cells are incorporated into totipotent cells (e.g., ES cells or oocytes), which are then handled as described above for the original methods.

Most commonly, the gene disruption procedures result in disruption of only one allele of a gene of interest. In these cases, animals bred as described to have the gene disruption in all their somatic and germ cells, will have only one allele disrupted, i.e., the animals will be heterozygous for the disrupted gene. Breeding of such a heterozygotes and appropriate selection procedures familiar to artisans in the field can then be used to derive animals that are homozygous for the disrupted gene. Naturally, such breeding procedures are not necessary where the gene disruption procedure described above resulted in disruption of both alleles of the gene of interest.

The above-described procedures have also been used to generate disruptions of genes other than the GT gene in species such as, without limitation, mice, sheep, and pigs Furthermore, in light of the fact that somatic cell procedures (as described above) have been successfully used to generate GTδ pigs as well as standard non-gene disrupted transgenic sheep and cattle [Wilmut et al. (1997) Nature 385:81-813; Kato et al. (1998) Science 282:2095-2098; Schnieke et al. (1997) Science 278: 2130-2133; Cibelli et al. (1998) Science 280: 1256-1258], the somatic cell-based procedures can readily be adapted for the generation of gene-disrupted (including GTδ) animals of a wide variety of species.

The following examples serve to illustrate, not limit, the invention.

EXAMPLES

Example 1

Materials and Methods

Preparation of Matrices Used for Implantation Experiments

For the experiments described in Examples 2-4 below, acellular dermal matrices (ADM) from human donors, wild type pigs, and GT6 pigs were produced using LifeCell's proprietary methodology. The methodology for making ADM from human donors (Alloderm) is described in detail below; the process used for making ADM from pig skin is essentially identical except as otherwise stated.

Human donor skin was obtained from various U.S. tissue banks and hospitals throughout the nation that collected skin samples using standard procedures from deceased donors after obtaining the consent from family members. Procured skin was placed in RPMI 1640 tissue culture media containing antibiotics (penicillin and streptomycin) and was shipped to LifeCell's facility in Branchburg, N.J., on wet ice, in the same media. On arrival, the temperature of the skin tissue container was measured and the skin tissue was discarded if the temperature was above 10° C. The RPMI 1640 media was changed under aseptic condition and the skin was stored at 4° C., while serological tests (e.g., for syphilis, HIV I and II, hepatitis B surface antigen, hepatitis C virus and HTLV I and II) were performed. The skin was then transferred to a prefreezing aqueous solution of 35% w/v maltodextrin. After 2 to 4 hours, the skin was frozen and stored in a −80° C. freezer until it was processed as described below.

Frozen skin was thawed at 37° C. in a water bath until no visible ice was left. The pre-freezing solution was drained before further processing, consisting of the following steps: (i) de-epidermization; (ii) de-cellularization; (iii) wash.

(i) De-epidermization: Skin epidermis was removed by incubating the tissue sample with gentle agitation in a de-epidermizing solution (1M NaCl, 0.5% w/v Triton X100, 10 mM EDTA) for 8-32 hours for human skin and 30-60 hour for porcine skin at room temperature. The epidermal layer was removed from dermis. The epidermis was discarded and the dermis retained for further processing.

(ii) De-cellularization: In order to remove cellular components, the dermis was rinsed for 5 to 60 minutes with a de-cellularizing solution (2% w/v sodium deoxycholate, 10 mM EDTA, 10 mM HEPES buffer, pH 7.8-8.2), and then incubated with gentle agitation in that solution for 12-30 hours at room temperature.

(iii) Wash: The washing regimen serves to wash out dead cells, cell debris, and residual chemicals used in the previous processing steps. The de-cellularized dermis was transferred to a first wash solution (phosphate buffered saline (PBS) containing 0.5% w/v Triton X-100 and 10 mM EDTA) which was then incubated with gentle agitation for 5 to 60 minutes at room temperature. The dermis was then subjected to three sequential washes in a second wash solution (PBS containing 10 mM EDTA) with gentle agitation at room temperature. The first two washes were short (15-60 minutes each) and the third wash was long (6-30 hours).

After the wash regimen, the resulting ADM were freeze-dried using standard methods. Immediately prior to implantation, the samples were rehydrated in normal saline, cut into appropriate sizes (about 1 cm$^2$), and then used for the experiments described in Examples 2-4.

Operative Procedure

Old World Primates (African green monkeys (*Ceropithecus aethiops*); 5-7 year-old males) were implanted with ADM made from either wild type pigs (XenoDerm™), human donors (Alloderm®), or GTδ pigs [Lai, L., et al. (2002)] (GalDerm™). The ADM were placed into four sub-dermal pockets created in their upper backs.

The ADM, which had been freeze dried, were prehydrated in excess saline for about 30 minutes. Each monkey was implanted with 1 piece of ADM per site (each piece being approximately 1 cm$^2$). Thus each animal received four implants of the same ADM, the four implants corresponding to four time points, i.e., day 0, day-7, day-21, and day-35. Three animals were implanted with each ADM (n=3). Implants with associated adherent host tissue were removed at each time point by excision of the sample material. Explants were bisected with a scalpel; half was placed in formalin fixative (and stored at 4° C.), and the other half was placed in sucrose cryoprotectant (and stored at 4° C.) for histological analysis.

Detection of αgal Epitopes

Detection of αgal epitopes in the ADM was done by direct immunohistology. AlloDerm, XenoDerm, and GalDerm, were immunostained with a monoclonal mouse IgG3 anti-αgal antibody. Antibody binding was detected using a horse-radish peroxidase (HRP)-conjugated goat anti-mouse IgG3 secondary antibody, and visualized with 3,3'-diaminobenzi-dine (DAB).

Histological Analysis

Histological analysis of the implanted material was done by standard hematoxylin and eosin (H&E) staining of formalin-fixed sections of each explant.

Serum Analysis

The occurrence of a humoral immune response to the implant was assessed by determining the titer of implant-specific antibody in the sera of the animals at various times after implantation. Blood was drawn at time points throughout the study, i.e., on day-0, day-7, day-21, and day-35. Serum was isolated and stored at −70° C. prior to analysis.

Serum dilutions were tested for relative level of antibody specific for antigens of implanted tissue via a modified sandwich ELISA procedure. Antibody titration curves were derived from serum samples obtained on days 7, 21, and 35 compared and curves were compared with values obtained with day-0 (pre-implant) serum samples.

ELISA plates were prepared as follows. Samples of the individual ADM used for implantation were freeze-dried and then powdered by cryofracture using a Spexfreezer™ mill (Spex Industries, Edison, N.J.). Each sample of powdered ADM was suspended in phosphate buffered saline (PBS) at a final concentration of 0.5 mg/mL. Aliquots (of 50 µL) of the suspensions were added to the wells of 96-well immulon ELISA plates and allowed to air dry. The powdered ADM were fixed to the well bottoms by adding 0.2% glutaraldehyde to the wells and incubating the plates for 30 minutes at room temperature. The plates were then washed and the well contents blocked with 0.2 M glycine. After further washing, bovine serum albumin (BSA; 1% in Tris-buffered saline (TBS)) was added to the wells to block non-specific protein-binding sites. Test sera obtained from the monkeys at the indicated timepoints were diluted in 1% BSA. After discarding the BSA solution used to block non-specific protein-binding sites, aliquots (50 µL) of serum dilutions were placed in the microtiter wells and incubated for 2 hours at room temperature. The plates were washed three times with TBS containing 0.1% Tween. After washing of the plates to remove unbound material in the added serum dilutions, an optimal dilution of goat anti-human IgG secondary antibody conjugated to alkaline phosphatase (Sigma, St. Louis, Mo.) was added to each well of the plate. The plates were incubated at room temperature for 1 hour and then washed five times with TBS containing 0.1% Tween. The pNPP (4-nitrophenyl phosphate) substrate was added to each of the wells, and the plates were incubated for 1 hour at room temperature to facilitate a color reaction. The optical density at 405 nm ($OD_{405}$) of each well was read using a microwell plate spectrophotometer. The $OD_{405}$ values were used to generate titration curves.

Example 2

Presence and Absence of αgal Epitopes in ADM

To assess the presence of αgal epitopes in implant materials, AlloDerm, XenoDerm, and GalDerm (FIGS. 1A, 1B, and 1C, respectively) were stained with a mouse IgG3 monoclonal anti-αgal antibody, a HRP-conjugated goat anti-mouse IgG3 secondary antibody, and the HRP substrate DAB. Controls to detect non-specific binding of the secondary antibody were included; these control samples were exposed to the secondary antibody only. The control for staining of GalDerm is shown in FIG. 1D. AlloDerm and XenoDerm samples were also counter-stained with hematoxylin. XenoDerm (FIG. 1B) showed diffuse staining with the anti-αgal antibody throughout the matrix coincident with edges of collagen bundles. On the other hand, no staining with the anti-αgal antibody was seen in AlloDerm (FIG. 1A). Similarly, GalDerm (FIG. 1C) showed no signal with the anti-αgal antibody above that obtained in the control sample (FIG. 1D). These results demonstrated the absence of αgal epitopes on GalDerm and AlloDerm and their presence on XenoDerm.

Example 3

Histological Analysis of Explants

Figure 2:
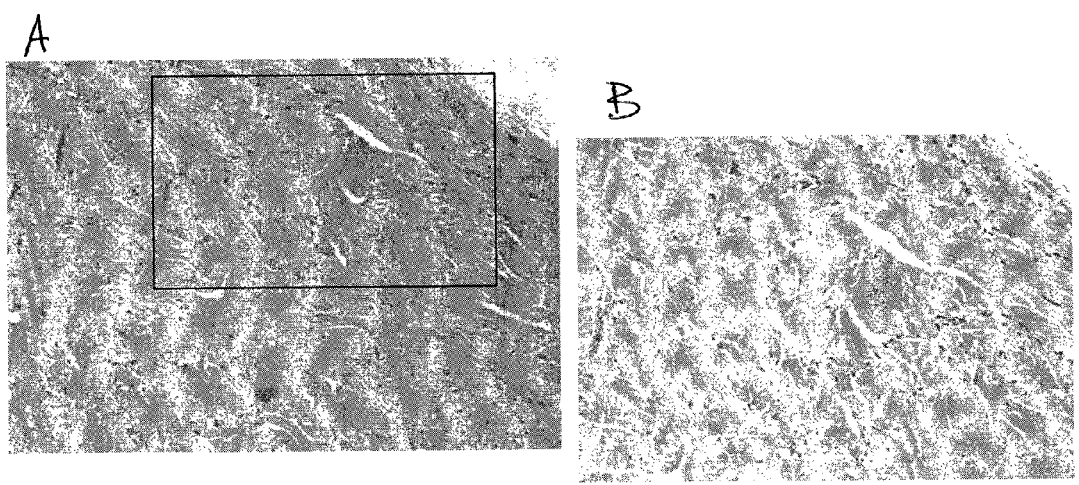
FIGS. 2A and B are photographs of a hematoxylin and eosin (H&E) stained AlloDerm sample removed from an African green monkey (Old World primate) 35 days after implantation in the monkey. Photographs were taken at 40× (FIG. 2A) and 100× (FIG. 2B) magnification. The field shown in FIG. 2B is indicated by a rectangle in FIG. 2A.
Figure 3:
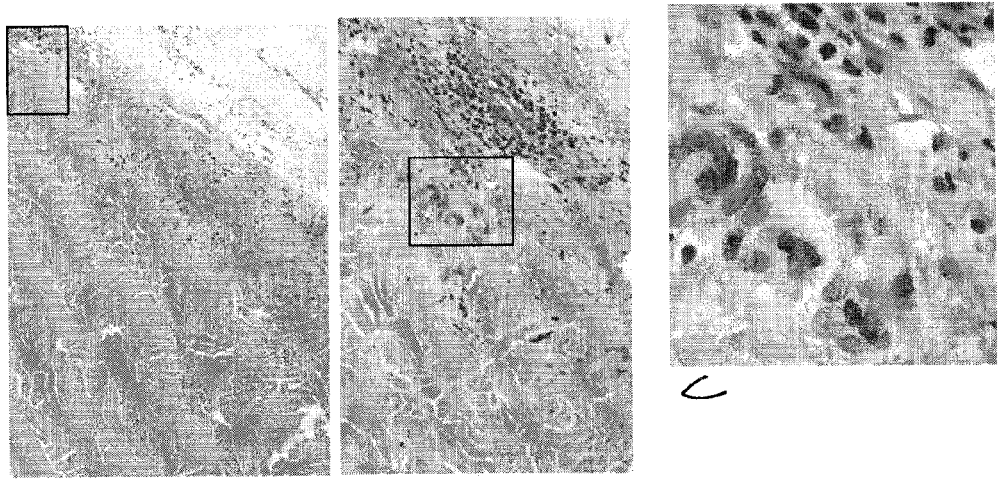
FIGS. 3A-C are photographs of a H&E stained XenoDerm sample removed from an African Green monkey (Old World primate) 35 days after implantation in the monkey. Photographs were taken at 40× (FIG. 3A), 100× (FIG. 3B), and (FIG. 3C) 400× magnification. The field shown in FIG. 3B is indicated by a rectangle in FIG. 3A and the field shown in FIG. 3C is indicated by a rectangle in FIG. 3B.
Figure 4:
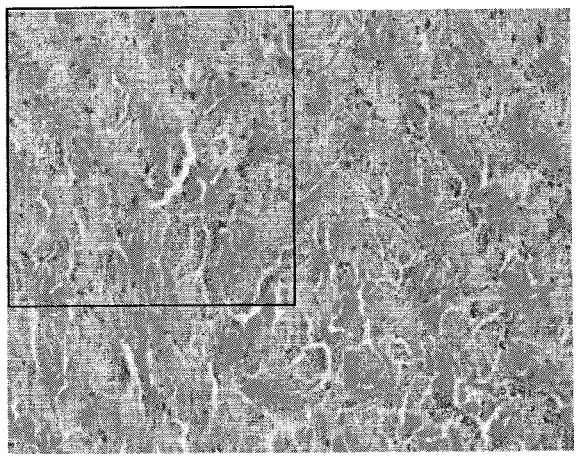
FIGS. 4A and B are photographs of a H&E stained Gal-Derm sample removed from an African Green monkey (Old World primate) 35 days after implantation in the monkey. Photographs were taken at 40× (FIG. 4A) and 100× (FIG. 4B) magnification. The field shown in FIG. 4B is indicated by a rectangle in FIG. 4A.
Figure 4:
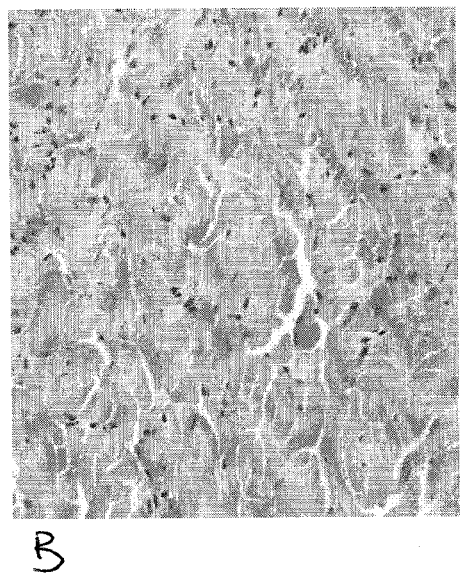

Histological evaluation of the implants 7 days after implantation revealed cellular infiltrates in the peripheral regions of all three types of ADM. Histological evaluation of the implants at day 35 after implantation showed significant differences between the three types of ADM. AlloDerm (FIGS. 2A and 2B) and GalDerm (FIGS. 4A and 4B) showed repopulation with fibroblast-like cells throughout the implants. On the other hand, in XenoDerm (FIGS. 3A, 3B and 3C) there were extensive cellular infiltrates in the peripheral region, these infiltrates being composed primarily of inflammatory cells, and there was no evidence of cellular repopulation of the interior of the implant.

Example 4

Analysis of Sera from Implant Recipients

Figure 5:
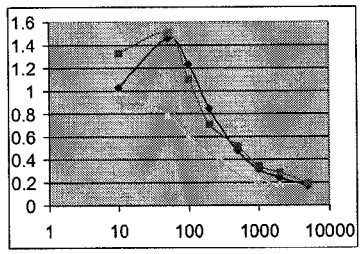
FIGS. 5A-C are a series of line graphs showing the titers of implant-specific IgG antibodies (as measured by ELISA) in the sera of individual monkeys (3 per group) at 0, 7, 21, and 35 days after implantation of XenoDerm™ (FIG. 5A), Gal-Derm™ (FIG. 5B), or AlloDerm® (FIG. 5C). $OD_{405}$ values are shown on the Y-axes and reciprocal values of serum dilutions (logarithmic scale) in the ELISA (enzyme-linked immunosorbent assay) are shown on the X-axes. Individual monkey-identifying numbers are indicated above each graph.
Figure 5:
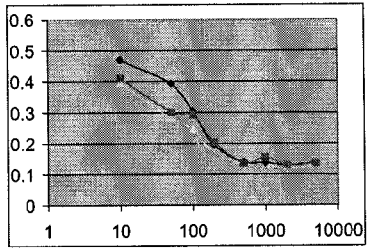
Figure 5:
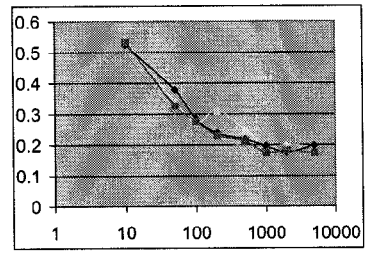
Figure 5:
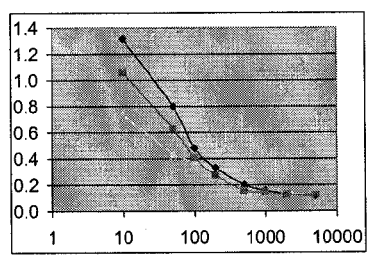
Figure 5:
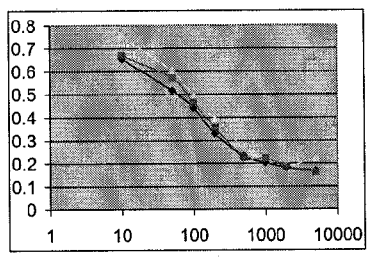
Figure 5:
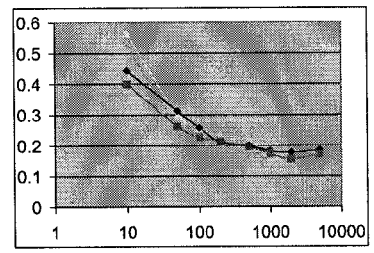
Figure 5:
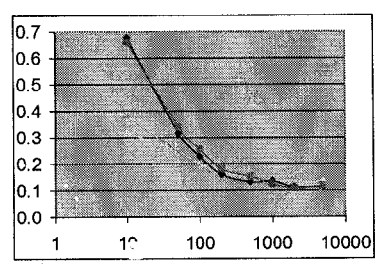
Figure 5:
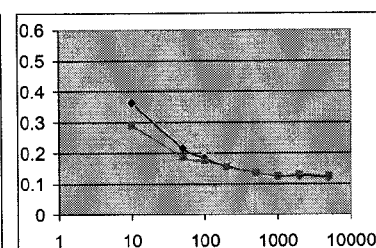
Figure 5:
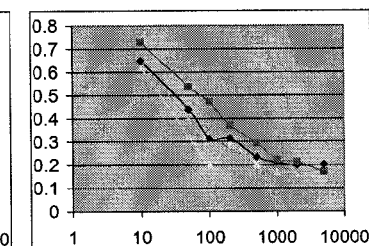

The presence of a humoral (antibody) immune response against implanted material in the test recipient animals was tested by measuring the production of tissue-specific antibodies in sera obtained from these animals. Antibody binding to the corresponding implant material was measured by a modified ELISA assay (see Example 1). The production of antibodies at various time points in serum samples was assessed by comparison with pre-transplant values. It is clear that sera from all the animals contained preformed ADM-binding antibodies, i.e., ADM-binding antibodies were detected in sera obtained on day 0 from all animals (FIG. 5). The serum dilution curves show clear increases in the titers of anti-XenoDerm IgG antibodies in sera obtained 21 days after implantation of XenoDerm (FIG. 5A). The levels of these antibodies remained elevated through the 35 day time point. In contrast, in monkeys implanted with GalDerm (FIG. 5B) and AlloDerm (FIG. 5C) there was no elevation in the titers of IgG ADM-binding antibodies (at any time point) compared to pre-implant IgG levels.

To further characterize the specificity of the antibodies in sera from XenoDerm-implanted animals that bound to XenoDerm in the ELISA, a competition ELISA in the presence or absence of αgal was performed. The binding to XenoDerm of antibodies in sera obtained at all three time points from all three monkeys implanted with XenoDerm was completely inhibited by 10 mM αgal (data not shown). These results indicate that: (a) antibodies in sera from XenoDerm-implanted animals that bound to XenoDerm were anti-αgal antibodies; and (b) in these animals there was no significant XenoDerm-specific antibody response to antigens other than αgal epitopes.

The data indicate in toto that the transplantation of XenoDerm into αgal deficient monkeys caused the monkeys to mount a systemic antibody response and that this antibody response is directed largely, if not exclusively, against αgal epitopes in the XenoDerm. GalDerm and AlloDerm implants, on the other hand, initiated no such antibody response.

A number of embodiments of the invention have been described. Nevertheless, it will be understood that various modifications may be made without departing from the spirit and scope of the invention. Accordingly, other embodiments are within the scope of the following claims.

What is claimed is:

1. An acellular tissue matrix comprising:
   a decellularized collagen-containing dermal tissue of a pig genetically modified to include a chromosomal genetic modification comprising a disruption of both alleles of an α-1,3 galactosyl transferase (αGT) gene such that tissues in the pig lack galactose α-1,3-galactose epitopes,
   wherein the acellular tissue matrix lacks epithelial basement membrane.

2. The acellular tissue matrix of claim 1, wherein the acellular tissue matrix is in non-particulate form.

3. The acellular tissue matrix of claim 1, wherein the acellular tissue matrix is in particulate form.

4. A method of making an acellular tissue matrix, the method comprising:
   (a) providing a collagen-containing tissue from a pig genetically modified to include a chromosomal genetic modification comprising a disruption of both alleles of an $\alpha$-1,3 galactosyl transferase ($\alpha$GT) gene so that tissues in the pig lack galactose $\alpha$-1,3-galactose epitopes; and
   (b) processing the tissue so as to render the tissue acellular and lacking an epithelial basement membrane, the processing resulting in the production of an acellular tissue matrix.

5. The method of claim 4, further comprising freezing the acellular tissue matrix.

6. The method of claim 4, further comprising freeze-drying the acellular tissue matrix.

7. The method of claim 4, further comprising:
   (a) pulverizing the acellular tissue matrix; or
   (b) rendering the acellular tissue matrix particulate in form.

8. The method of claim 4, wherein the process comprises removing and discarding epidermis.

9. A method of treatment, the method comprising:
   (a) identifying a mammalian subject as having an organ or tissue in need of repair or amelioration; and
   (b) placing a composition comprising the acellular tissue matrix of claim 1 in or on the organ or tissue.

10. The method of claim 9 wherein the subject is a human.

11. The method of claim 9, wherein the acellular tissue matrix is in non-particulate form.

12. The method of claim 9, wherein the acellular tissue matrix is in particulate form.

13. The method of claim 9, further comprising administration to the subject of at least one agent selected from a cell growth factor, an angiogenic factor, a differentiation factor, a cytokine, a hormone, and a chemokine.

14. The method of claim 13, wherein the at least one agent is in the composition placed in the subject.

15. The method of claim 13, wherein the administration comprises injecting or infusing the at least one agent into the mammalian subject separately from the composition.

16. The method of claim 9, wherein the organ or tissue of the subject is selected from at least one of skin, bone, cartilage, meniscus, dermis, myocardium, periosteum, artery, vein, stomach, small intestine, large intestine, diaphragm, tendon, ligament, neural tissue, striated muscle, smooth muscle, bladder, urethra, ureter, and gingiva.

17. The method of claim 9, wherein the organ or tissue of the subject is abdominal wall fascia.

18. The method of claim 9, wherein the composition further comprises demineralized bone powder.

19. The method of claim 16, wherein the organ or tissue of the subject is gingiva, and wherein the gingiva is, or is proximal to, receding gingiva.

20. The method of claim 16, wherein the organ or tissue of the subject is gingiva, and wherein the gingiva comprises a dental extraction socket.

\* \* \* \* \*